United States Patent
Inamori et al.

(10) Patent No.: US 6,444,649 B1
(45) Date of Patent: Sep. 3, 2002

(54) SOLID DISPERSION CONTAINING SIALIC ACID DERIVATIVE

(75) Inventors: Takeshi Inamori; Chikako Takahashi, both of Hazaki-machi; Yoshiyuki Fujimura, Yokohama, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/646,873

(22) PCT Filed: Apr. 9, 1999

(86) PCT No.: PCT/JP99/01907

§ 371 (c)(1),
(2), (4) Date: Dec. 27, 2000

(87) PCT Pub. No.: WO99/52931

PCT Pub. Date: Oct. 21, 1999

(30) Foreign Application Priority Data

Apr. 10, 1998 (JP) .......................................... 10-098899

(51) Int. Cl.[7] .............................................. A61K 31/70
(52) U.S. Cl. ........................................................ 514/42
(58) Field of Search ........................................... 514/42

(56) References Cited

U.S. PATENT DOCUMENTS 4,229,441 A    10/1980    Bugianesi et al.

FOREIGN PATENT DOCUMENTS

| | | |
|---|---|---|
| JP | 55-89298 | 7/1980 |
| JP | 58-77811 | 5/1983 |
| JP | 61243096 | 10/1986 |
| JP | 61282390 | 12/1986 |
| JP | 62209094 | 9/1987 |
| JP | 62265229 | 11/1987 |
| JP | 63-41492 | 2/1988 |
| JP | 63-41494 | 2/1988 |
| JP | 63-63697 | 3/1988 |
| JP | 63-68526 | 3/1988 |
| JP | 64-52794 | 2/1989 |
| JP | 1-93529 | 4/1989 |
| JP | 1-190693 | 7/1989 |
| JP | 3-77898 | 4/1991 |
| JP | 3-81287 | 4/1991 |
| JP | 3-151398 | 6/1991 |
| JP | 7-228592 | 8/1995 |
| JP | 9-2957 | 1/1997 |
| WO | 93/10134 | 5/1993 |
| WO | 94/03469 | 2/1994 |

OTHER PUBLICATIONS

English Language Abstract of JP 1–190693 (1989).
English Language Abstract of JP 1–93529 (1989).
English Language Abstract of JP 3–151398 (1991).
English Language Abstract of JP 3–77898 (1991).
English Language Abstract of JP 3–81287 (1991).
English Language Abstract of JP 7–228592 (1995).
English Language Abstract of JP 9–2957 (1997).
English Language Abstract of JP 58–77811 (1983).
English Language Abstract of JP 61–243096 (1986).
English Language Abstract of JP 61–282390 (1986).
English Language Abstract of JP 62–209094 (1987).
English Language Abstract of JP 62–265229 (1987).
English Language Abstract of JP 63–41492 (1988).
English Language Abstract of JP 63–41494 (1988).
English Language Abstract of JP 63–63697 (1998).
English Language Abstract of JP 63–68526 (1988).
English Language Abstract of JP 64–52794 (1989).
Shigeru Yakou et al., "Dissolution and Bioavailability of Phenytoin in Phenytoin–Polyvinylpyrrolidone–Sodium. Deoxycholate Coprecipitate", Chem. Pharm. Bull., vol. 34, pp. 3408–3414 (1986).
Win Loung Chiou et al., "Oral Absorption of Griseofulvin in Dogs: Increased Absorption via Solid Dispersion in Polyethylene Glycol 6000" Journal of Pharmaceutical Sciences, vol. 59, No. 7, pp. 937–942 (1970).
Takao Mizumoto et al., "Improving Dissolution Rate of Slightly Soluble Drug Nifedipine by Procedures of Roll Mixing with Polyvinylpyrrolidone", Pharmaceutics (Yakuzaigaku), vol. 45, No. 4, pp. 291–297 (1985).
Toshiya Kai et al., "Oral Absorption Improvement of Poorly Soluble Drug Using Solid Dispersion Technique", Chem. Pharm. Bull., vol. 44, No. 3, pp. 568–571 (1996).
Taiji Kato et al., "Sialosyl Cholesterol Induces Morphological and Biochemical Differentiations of Glioblasts without Intracelluar Cyclic AMP Level Rise", Brain Research, vol. 438, pp. 277–285 (1988).

*Primary Examiner*—Raymond Henley, III
(74) *Attorney, Agent, or Firm*—Greenblum & Bernstein, P.L.C.

(57) ABSTRACT

The invention provides a medicament comprising a sialic acid derivative represented by the following formula and have superior solubility and absorbability. A solid dispersion comprising a water-soluble macromolecule such as hydroxypropylmethylcellulose and a sialic acid derivative dispersed in the water-soluble macromolecule and represented by the following formula (I):

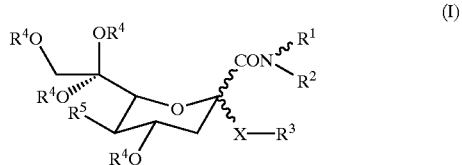

[$R^1$ represents a steroid compound residue; $R^2$ represents hydrogen atom or a $C_1$–$C_4$ alkyl group, $R^3$ represents a $C_1$–$C_{15}$ alkyl group etc.; X represents an oxygen atom or a sulfur atom], e.g., 3α-[N-(5-acetamido-3,5-dideoxy-2-O-methyl-α-D-glycero-D-galacto-2-noneuropyranosonyl)amino]cholestane.

18 Claims, 3 Drawing Sheets

SOLID DISPERSION CONTAINING SIALIC ACID DERIVATIVE

TECHNICAL FIELD

The present invention relates to a solid dispersion containing a substance useful for therapeutic and/or preventive treatment of various diseases resulting from impairment of cholinergic nerve cells, and a pharmaceutical composition containing said solid dispersion.

BACKGROUND ART

In order to utilize hardly soluble and/or hardly absorbable substances as a pharmaceutical preparation, it has been attempted to improve their solubility and absorbability. As a physicochemical method for such attempt, amorphization is known. In this technique, crystalline structures of the substances are destroyed and pulverized into a size of molecular level. An example of amorphized states includes solid dispersion. The solid dispersion contains a substance dispersed in a size of molecular level in a carrier, and the dispersion is such a state that a solid is dissolved in a solid. In the solid dispersion, a dispersed substance does not contact with each other. and accordingly, crystallization hardly occurs and stability of the substance in the amorphized state is generally improved.

It is known that solubility and absorbability of a hardly soluble compound can be improved by dispersing the substance in a water-soluble macromolecule to form an amorphous solid dispersion. For example, Japanese Patent Unexamined Publication (Kokai) 58-77811/1983 discloses that solubility and absorbability of nifedipine, which is useful as a therapeutic drug for angina pectoris, can be improved by dispersing said drug in hydroxypropylmethylcellulose to form a solid dispersion. As methods for preparing a solid dispersion, there are known, for example, the solvent method wherein a substance and a water-soluble macromolecule are dissolved in a suitable solvent, and then the solvent is removed (Chem. Pharm. Bull., 34 (8), 3408 (1986)), the fusion method wherein a substance and a water-soluble macromolecule are fused and solidified by cooling (J. Pharm. Sci., 59, 937 (1970)), the mixed grinding method wherein a substance and a water-soluble macromolecule are mixed and pulverized by a ball mill or the like (Yakuzaigaku (Pharmaceutics), 45 (4), 291 (1985)), the spray drying method wherein a solution of a drug and a water-soluble macromolecule is spray-dried (Chem. Pharm. Bull., 44 (3), 568 (1996)) and the like.

Gangliosides, which are glycosphingolipids including sialic acid, are components of biomembranes and abundantly contained in brains of higher animals. Variety of functions of gangliosides have recently been reported. Since gangliosides are present highly locally in membranes of the nerve system, their role in the nerve system have been focused. Sialic acid is an important component of gangliosides, and various sialic acid derivatives have been synthesized to investigate correlation between sialic acid and the functions of gangliosides and from a viewpoint of clinical applications (Japanese Patent Unexamined Publication Nos. 55-89298/1980, 61-243096/1986, 61-282390/1986, 63-41492/1988, 63-41494/1988, 63-63697/1988, 63-68526/1988, 64-52794/1989, 1-190693/1989, 3-151398/1991, WO93/10134, WO094/03469 etc.). Some reports have also been made on the activity of sialic acid derivatives (Japanese Patent Unexamined Publication Nos. 62-265229/1987, 1-93529/1989, 3-77898/1991, 3-81287/1991, and Brain Research, 438, 277-285 (1988)).

The applicants of the present application discovered previously sialic acid derivatives having an activity for activating an acetylcholine synthetase, i.e., choline acetyltransferase (ChAT) (Japanese Patent Unexamined Publication No. 7-228592/1995). These sialic acid derivatives have actions of improving central nervous system disorders such as dysmnesia in senile dementia including Alzheimer's disease and peripheral nerve system disorders such as diabetic neuropathy, and therefore they are very useful as active ingredients of drugs. Since the compounds of said invention activate ChAT activity in cholinergic nerve cells, their prophylactic or therapeutic efficacy for dementia, dysmnesia and symptoms resulting therefrom is expected. Specifically, they are considered to be useful for prophylactic and therapeutic treatments of senile dementia including Alzheimer's disease; cerebrovascular dementia accompanying apoplectic stroke, encephalorrhagy, cerebral infarction etc.; and dysmnesia, hypoprosexia, allophasis, hypobulia, emotional disorder, hallucination, paranoid state, behavioral abnormality and the like resulting from head injury, postencephalitis, cerebral paralysis, Huntington disease, Pick's disease, Down's syndrome, Parkinson's disease etc. They are also useful for prophylactic and therapeutic treatments of tardive dyskinesia; glaucoma; dysgryphia; peripheral nerve disorders of motor nerve, sensory nerve, autonomic nerve etc. including traumatological and inflammatory neuropathiesi alcoholic nerve disorder, drug induced nerve disorder caused by carcinostatic agents etc., metabolic nerve disorder resulting from diabetes mellitus etc. or idiopathic peripheral nerve disorder induced by carcinostatic agents etc.; facial nerve palsy: ischiadic nerve palsy; myelopathic muscular atrophy; muscular dystrophy; myasthenia gravis; multiple sclerosis; a myotrophic lateral sclerosis; acute disseminated encephalomyelitis; Guillain-Barre syndrome: postvaccinal encephalitis; subacute myelo-optic neuropathy (SMON disease) and the like. However, these sialic acid derivatives are almost insoluble in water and hardly absorbable, and for this reason, drugs prepared by ordinary formulation techniques fail to sufficiently exert efficacy.

DISCLOSURE OF THE INVENTION

An object of the present invention is to provide medicaments which comprise a sialic acid derivatives disclosed in Japanese Patent Unexamined Publication No. 7-228592/1995 and can sufficiently take sufficient effects. More specifically, the object of the present invention is to provide medicaments which achieve superior solubility and absorbability of the sialic acid derivative.

The inventors of the present invention made extensive studies to achieve the foregoing object. As a result, they found that the object was achievable by preparing a solid dispersion in which an active ingredient such as the aforementioned sialic acid derivatives or salts thereof in a water-soluble macromolecule, and that medicaments superior in solubility and absorbability of the active ingredient and capable of exerting high efficacy were successfully provided. The present invention was accomplished on the basis of these findings.

The present invention thus provides a solid dispersion which comprises a water-soluble macromolecule and a substance dispersed in the water-soluble macromolecule, wherein said substance is selected from the group consisting of a sialic acid derivative represented by the following general formula (I) and a salt thereof, and a hydrate thereof and a solvate thereof:

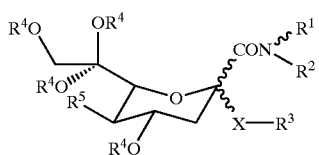

(I)

[in the above general formula (I), $R^1$ represents a steroid compound residue, $R^2$ represents hydrogen atom or a $C_1$–$C_4$ alkyl group, $R^3$ represents a $C_1$–$C_{15}$ alkyl group,

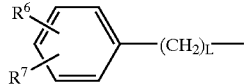

{in the formula, $R^6$ and $R^7$ independently represent hydrogen atom, a halogen atom, a $C_1$–$C_4$ alkyl group, hydroxyl group, $R^8O$— (in the formula, $R^8$ represents a $C_1$–$C_4$ alkyl group, phenyl group or a phenyl-($C_1$–$C_3$) alkyl group), nitro group, amino group, a $C_1$–$C_4$ alkylamino group, a $C_2$–$C_8$ dialkylamino group or $R^9O$—CO— (in the formula, $R^9$ represents hydrogen atom, a $C_1$–$C_4$ alkyl group, phenyl group or a phenyl-($C_1$–$C_3$) alkyl group), and symbol "L" represents an integer of from 0 to 6}, $R^{10}O(CH_2)m$— (in the formula, $R^{10}$ represents hydrogen atom; a $C_1$–$C_4$ alkyl group; a phenyl group which may have one or more substituents selected from the group consisting of a $C_1$–$C_4$ alkyl group, a halogen atom, hydroxyl group, nitro group, amino group, and a carboxyl group; or a phenyl-($C_1$–$C_3$) alkyl group which may have one or more substituents selected from the group consisting of a $C_1$–$C_4$ alkyl group, a halogen atom, hydroxyl group, nitro group, amino group, and carboxyl group, and symbol "m" represents an integer of from 2 to 6), or $(R^{11})(R^{12})N$—$(CH_2)_n$— {in the formula, $R^{11}$ represents hydrogen atom or a $C_1$–$C_4$ alkyl group, $R^{12}$ represents hydrogen atom; a $C_1$–$C_4$ alkyl group; a $C_2$–$C_7$ acyl group; a $C_1$–$C_4$ alkylsulfonyl group; a phenylsulfonyl group which may have one or more substituents selected from the group consisting of a $C_1$–$C_4$ alkyl group, halogen atom, hydroxyl group, nitro group, amino group, and a carboxyl group; or $R^{13}O$—CO— (in the formula, $R^{13}$ represents a $C_1$–$C_4$ alkyl group, phenyl group or a phenyl-($C_1$–$C_3$) alkyl group) and symbol "n" represents an integer of from 2 to 6}, $R^4$ represents hydrogen atom or a $C_2$–$C_7$ acyl group, $R^5$ represents $R^{14}O$— (in the formula, $R^{14}$ represents hydrogen atom or a $C_2$–$C_7$ acyl group) or $R^{15}NH$— {in the formula, $R^{15}$ represents a $C_2$–$C_7$ acyl group: $R^{16}O(CH_2)_p$—CO— (in the formula, $R^{16}$ represents hydrogen atom, a $C_1$–$C_6$ alkyl group, phenyl group, or a phenyl-($C_1$–$C_3$) alkyl group, and p represents an integer of from 0 to 4); a $C_7$–$C_{11}$ aroyl group which may have one or more substituents selected from the group consisting of a $C_1$–$C_4$ alkyl group, a halogen atom, hydroxyl group, nitro group, amino group, and a carboxyl group; a phenyl-($C_1$–$C_3$) alkylcarbonyl group which may have one or more substituents selected from the group consisting of a $C_1$–$C_4$ alkyl group, a halogen atom, hydroxyl group, nitro group, amino group, and a carboxyl group; a $C_1$–$C_4$ alkylsulfonyl group; or a phenylsulfonyl group which may have one or more substituents selected from the group consisting of a $C_1$–$C_4$ alkyl group, a halogen atom, hydroxyl group, nitro group, amino group, and a carboxyl group}, and X represents an oxygen atom or a sulfur atom].

As preferred embodiments of the present invention, there are provided the aforementioned solid dispersion wherein $R^1$ represents

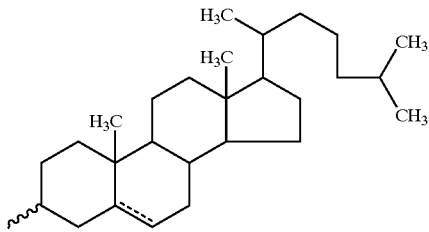

(in the formula,/=== represents a single bond or a double bond); the aforementioned solid dispersion, wherein $R^1$ represents

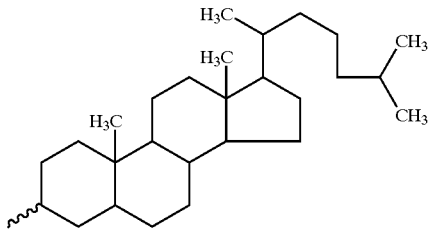

and the aforementioned solid dispersion, wherein $R^1$ represents

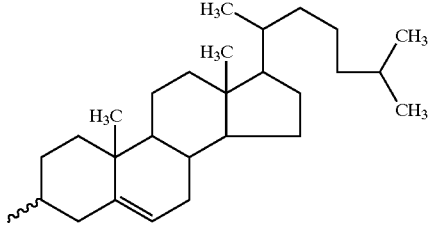

in the sialic acid derivative and a salt thereof, and a hydrate thereof and a solvate thereof.

As other preferred embodiments of the present invention, there are provided the aforementioned solid dispersion wherein, as for the substance selected from the sialic acid derivative and a salt thereof, and a hydrate thereof and a solvate thereof, $R^2$ represents hydrogen atom or methyl group; the aforementioned solid dispersion, wherein $R^2$ represents hydrogen atom; the aforementioned solid dispersion, wherein $R^3$ represents a $C_1$–$C_8$ alkyl group,

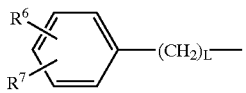

{in the formula, $R^6$ and $R^7$ independently represent hydrogen atom, a halogen atom, or $R^9O$—CO— (in the formula, $R^9$ represents hydrogen atom or a $C_1$–$C_4$ alkyl group), and symbol "L" represents an integer of from 0 to 3}, $R^{10}O$ $(CH_2)_m$— (in the formula, $R^{10}$ represents hydrogen atom, a $C_1$–$C_4$ alkyl group, phenyl group, or a phenyl-($C_1$–$C_3$) alkyl group, and symbol "m" represents an integer of from 2 to 4), or $(R^{11})(R^{12})N$—$(CH_2)_n$— {in the formula, $R^{11}$ represents hydrogen atom, $R^{12}$ represents hydrogen atom, a $C_2$–$C_7$, acyl group, a $C_1$–$C_4$ alkylsulfonyl group or $R^{13}O$—CO— (in the formula, $R^{13}$ represents a phenyl-($C_1$–$C_3$) alkyl group) and symbol "n" represents an integer of from 2 to 4};

and the aforementioned solid dispersion, wherein $R^3$ represents a $C_1$–$C_8$ alkyl group or

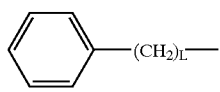

(in the formula, symbol "L" represents an integer of from 0 to 3).

As further preferred embodiments of the present invention, as for the substance selected from the sialic acid derivative and a salt thereof, and a hydrate thereof and a solvate thereof, there are provided the aforementioned solid dispersion, wherein $R^3$ represents a $C_1$–$C_3$ alkyl group; the aforementioned solid dispersion, wherein $R^4$ represents hydrogen atom or acetyl group; the aforementioned solid dispersion, wherein $R^4$ represents hydrogen atom; the aforementioned solid dispersion, wherein $R^5$ represents $R^{14}$O— (in the formula, $R^{14}$ represents hydrogen atom or acetyl group) or $R^{15}$NH— {in the formula, $R^{15}$ represents a $C_2$–$C_7$ acyl group, $R^{16}$O(CH$_2$)$_p$—CO— (in the formula, $R^{16}$ represents hydrogen atom, a $C_1$–$C_4$ alkyl group or a phenyl-($C_1$–$C_3$) alkyl group, and symbol "p" represents an integer of from 0 to 4), a $C_7$–$C_{11}$ aroyl group, a $C_1$–$C_3$ alkylsulfonyl group or a phenylsulfonyl group}; the aforementioned solid dispersion, wherein $R^5$ represents $R^{14}$O— (in the formula, $R^{14}$ represents hydrogen atom) or $R^{15}$NH— {in the formula, $R^{15}$ represents a $C_2$–$C_5$ acyl group, $R^{16}$O(CH$_2$)$_p$—CO— (in the formula, $R^{16}$ represents hydrogen atom and symbol "p" represents 1)}; the aforementioned solid dispersion, wherein $R^{15}$ represents $R^{15}$NH—(in the formula, $R^{15}$ represents acetyl group); and the aforementioned solid dispersion, wherein X represents oxygen atom.

As particularly preferred embodiments, there are provided the aforementioned solid dispersion, wherein the sialic acid derivative is 3 α-[N-(5-acetamido-3,5-dideoxy-2-O-methyl-α-D-glycero-D-galacto-2-noneuropyranosonyl)amino]cholestane; the aforementioned solid dispersion, which comprises the aforementioned substance in substantially amorphous state; and the aforementioned solid dispersion, which does not substantially comprise said substance in crystallized state. As another aspect, there is provided a pharmaceutical composition comprising the aforementioned solid dispersion and a pharmaceutically acceptable carrier.

BEST MODE FOR CARRYING OUT THE INVENTING

Figure 1:
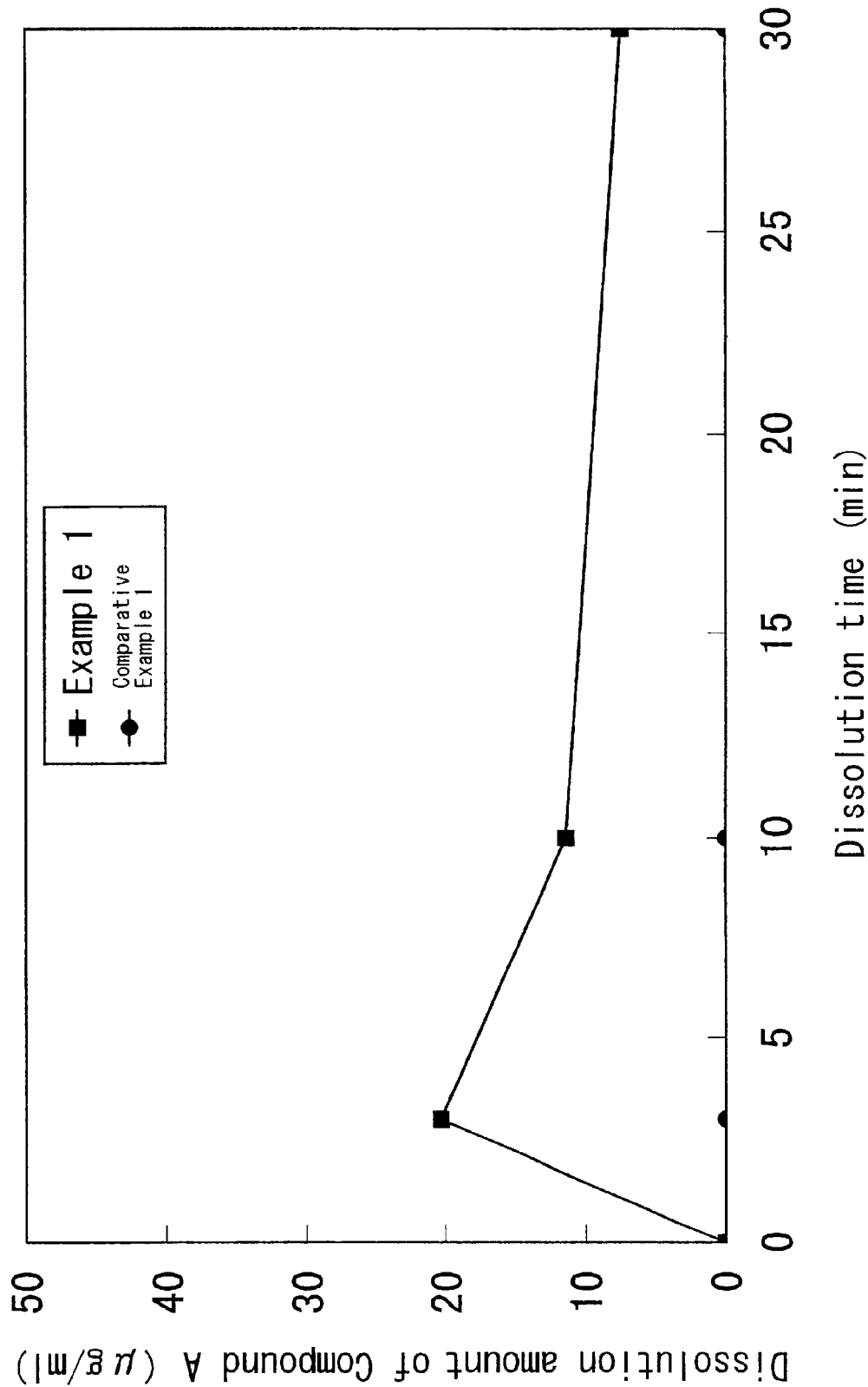
FIG. 1 shows results of a dissolution test of a solid dispersion of the present invention. The results shown in the figure are averages of experiments performed in triplicate. The line with ■ represents the results obtained from a solid dispersion of the present invention (Example 1); and the line with □ from the solid powder of Comparative Example 1.

The sialic acid derivative contained in the solid dispersion of the present invention is represented by the aforementioned general formula (I). Examples of the $C_1$–$C_4$ alkyl group defined in the aforementioned general formula (I) include methyl group, ethyl group, n-propyl group, i-propyl group, n-butyl group, t-butyl group and the like. Examples of the $C_1$–$C_{15}$ alkyl group include methyl group, ethyl group, n-propyl group, i-propyl group, n-butyl group, t-butyl) group, n-pentyl group, n-hexyl group, n-heptyl group, n-octyl group, n-decyl group, n-pentadecyl group and the like. Examples of the $C_1$–$C_6$ alkyl group include those $C_1$–$C_6$ alkyl groups exemplified above for the $C_1$–$C_{15}$ alkyl group. Examples of the halogen atom include fluorine atom, chlorine atom, bromine atom and the like. Examples of the phenyl-($C_1$–$C_3$) alkyl group include benzyl group, phenethyl group and the like. Examples of the $C_2$–$C_7$ acyl group include acetyl group, propionyl group, butyryl group, valeryl group, benzoyl group and the like. Examples of the $C_1$–$C_4$ alkylsulfonyll group include methylsulfonyl group, ethylsulfonyl group, n-propylsulfonyl group, n-butylsulfonyl group and the like.

Further, examples of the $C_1$–$C_4$ alkylamino group include methylamino group, ethylamino group, butylamino group and the like. Examples of the $C_2$–$C_8$ dialkylamino group include dimethylamino group, diethylamino group, dibutylamino group and the like. Examples of the $C_7$–$C_{11}$ aroyl group include benzoyl group, toluoyl group, naphthoyl group and the like. Examples of the phenyl-($C_1$–$C_3$) alkylcarbonyl group include benzylcarbonyl group. phenylethylcarbonyl group, phenylpropylcarbonyl group and the like.

A specific example of the steroid compound residue defined by $R^1$ in the formula (I) includes a group represented by the following formula:

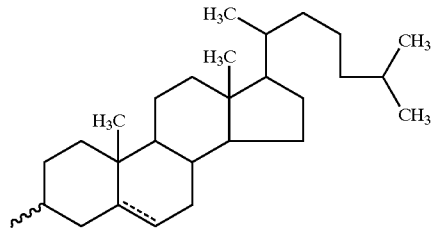

(in the formula, ==== represents a single bond or a double bond, and the steric configuration in the 3-position of the steroid skeleton is in either α-configuration or β-configuration).

A preferred example of $R^1$ include a steroid compound residue represented by the following formula:

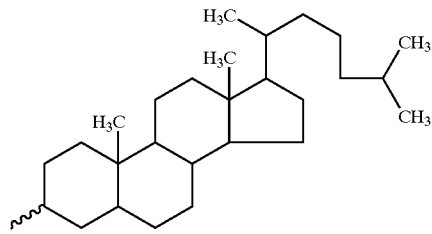

$R^2$ is preferably hydrogen atom or a methyl group, and hydrogen atom is most preferred. $R^3$ is preferably a $C_1$–$C_8$ alkyl group,

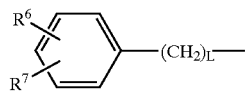

{in the formula, $R^6$ and $R^7$ independently represent hydrogen atom, a halogen atom or $R^9O$—CO— (in the formula, $R^9$ represents hydrogen atom or a $C_1$–$C_4$ alkyl group), and symbol "L" represents an integer of from 0 to 3}, $R^{10}O$ $(CH_2)_m$— (in the formula, $R^{10}$ represents hydrogen atom, a $C_1$–$C_4$ alkyl group, phenyl group, or a phenyl-$(C_1$–$C_3)$ alkyl group, and symbol "m" represents an integer of from 2 to 4), or $(R^{11})(R^{12})N$—$(CH_2)_n$— {in the formula, $R^{11}$ represents hydrogen atom, $R^{12}$ represents hydrogen atom, a $C_2$–$C_7$ acyl group, a $C_1$–$C_4$ alkylsulfonyl group or $R^{13}O$—CO— (in the formula, $R^{13}$ represents a phenyl-$(C_1$–$C_3)$ alkyl group) and symbol "n" represents an integer of from 2 to 4}, more preferably a $C_1$–$C_8$ alkyl group or

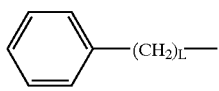

(in the formula, symbol "L" represents an integer of from 0 to 3), and a $C_1$–$C_3$ alkyl group is most preferred.

$R^4$ is preferably hydrogen atom or acetyl group, and hydrogen atom is most preferred. $R^5$ is preferably $R^{14}O$— (in the formula, $R^{14}$ represents hydrogen atom or acetyl group) or $R^{15}NH$— {in the formula, $R^{15}$ represents a $C_2$–$C_5$ acyl group, $R^{16}O(CH_2)_p$—CO— (in the formula, $R^{16}$ represents hydrogen atom, a $C_1$–$C_4$ alkyl group, or a phenyl-$(C_1$–$C_3)$ alkyl group, and symbol "p" represents an integer of from 0 to 4), a $C_7$–$C_{11}$ aroyl group, a $C_1$–$C_4$ alkylsulfonyl group, or a phenylsulfonyl group}}, more preferably $R^{14}O$— (in the formula, $R^{14}$ represents hydrogen atom) or $R^{15}NH$— {in the formula, $R^{15}$ represents a $C_2$–$C_5$ acyl group, $R^{16}O(CH_2)_p$—CO— (in the formula, $R^{16}$ represents hydrogen atom, and symbol "p" represents 1)}, most preferably $R^{15}NH$— (in the formula, $R^{15}$ represents acetyl group). X is most preferably an oxygen atom.

Specific examples of the substituents defined in the aforementioned general formula (I) and specific examples of the sialic acid derivatives represented by the formula (I) are mentioned in Japanese Patent Unexamined Publication No. 7-228592/1995. Other than the sialic acid derivatives having the substituents exemplified above, those specifically disclosed in Japanese Patent Unexamined Publication No. 7-228592/1995 are also preferably used for the solid dispersion of the present invention. However, the sialic acid derivatives which can be used for the solid dispersion of the present invention are not limited to those mentioned above, and it should be understood that any derivatives falling within the scope of the general formula (I) can be utilized.

Most preferred sialic acid derivatives include 3 α-[N-(3-deoxy-2-O-methyl-α-D-glycero-D-galacto-2-noneuropyranosonyl)amino]cholestane (α-isomer of Compound No. 367 mentioned in Japanese Patent Unexamined Publication No. 7-228592/1995, Table 5), 3α-[N-(3-deoxy-2-O-methyl-α-D-glycero-D-galacto-2-noneuropyranosonyl)amino]-5-cholestene (α-isomer of Compound No. 507 mentioned in Japanese Patent Unexamined Publication No. 7-228592/1995, Table 7), 3 α-[N-(5-acetamido-3,5-dideoxy-2-O-methyl-α-D-glycero-D-galacto-2-noneuropyranosonyl)amino] cholestane (α-isomer of Compound No. 4 mentioned in Japanese Patent Unexamined Publication No. 7-228592/1995, Table 1), 3 α-[N-(5-acetamido-3,5-dideoxy-2-O-phenyl-α-D-glycero-D-galacto-2-noneuropyranosonyl)amino] cholestane (α-isomer of Compound No. 19 mentioned in Japanese Patent Unexamined Publication No. 7-228592/1995, Table 1), 3 α-[N-(5-acetamido-3,5-dideoxy-2-O-benzyl-α-D-glycero-D-galacto-2-noneuropyranosonyl)amino] cholestane (α-isomer of Compound No. 21 mentioned in Japanese Patent Unexamined Publication No. 7-228592/1995, Table 1), 3 α-[N-(5-acetamido-3,5-dideoxy-2-O-methyl-α-D-glycero-D-galacto-2-noneuropyranosonyl)amino]-5-cholestene (α-isomer of Compound No. 234 mentioned in Japanese Patent Unexamined Publication No. 7-228592/1995, Table 1), 3 α-[N-(5-acetamido-3,5-dideoxy-2-S-phenyl-2-thio-α-D-glycero-D-galacto-2-noneuropyranosonyl)amino] cholestane (α-isomer of Compound No. 260 mentioned in Japanese Patent Unexamined Publication No. 7-228592/1995, Table 2), 3 α-[N-(5-acetamido-3,5-dideoxy-2-O-methyl-β-D-glycero-D-galacto-2-noneuropyranosonyl)amino] cholestane (α-isomer of Compound No. 268 mentioned in Japanese Patent Unexamined Publication No. 7-228592/1995, Table 3), and 3 α-[N-(5-acetamido-3,5-dideoxy-2-O-benzyl-β-D-glycero-D-galacto-2-noneuropyranosonyl)amino]cholestane (α-isomer of Compound No. 281 mentioned in Japanese Patent Unexamined Publication No. 7-228592/1995, Table 3). However, the sialic acid derivatives of the general formula (I) which can be used for the solid dispersion of the present invention are not limited to these examples.

Examples of salts formed with the carboxyl groups of the compounds represented by the general formula (I) include, for example, salts with alkali metals such as sodium or potassium, and salts with ammonia, organic amines such as tris(hydroxymethyl)aminomethane, N,N-bis(hydroxyethyl) piperazine, 2-amino-2-methyl-1-propanol, ethanolamine, N-methylglucamine, and L-glucamine.

Examples of salts formed with the compounds represented by the general formula (I) include, for example, inorganic acid salts such as hydrochlorides, hydrobromides, hydroiodides, sulfates, and phosphates, and organic acid salts such as oxalates, maleates, fumarates, lactates, malates, citrates, tartrates, benzoates, methanesulfonates and camphorsulfonates. However, the salts which can be used for the solid dispersion of the present invention are not limited to these examples, and any of physiologically acceptable salts can be utilized.

The compound of the aforementioned formula (I) or a salt thereof may exist in the forms of a hydrate or a solvate, and therefore, the hydrate or the solvate can also be used for the manufacture of the solid dispersion of the present invention. Solvents for forming the solvates are not particularly limited, and include, for example, methanol, ethanol, isopropanol, acetone, ethyl acetate, methylene chloride and the like. Further, the compounds of the aforementioned formula (I) have one or more asymmetric carbon atoms, and many isomers thereof may exist. Any of such isomers can be used for the manufacture of the solid dispersion of the present invention. The compounds falling within the aforementioned general formula (I) can be produced according to the method described in Japanese Patent Unexamined Publication No. 7-228592/1995 or analogous methods.

The types of the water-soluble macromolecules used for the manufacture of the solid dispersion of the present invention are not particularly limited, and any kinds of macromolecules may be used so long as they are pharmaceutically acceptable. Examples include, for example, hydroxypropylmethylcellulose, hydroxypropylcellulose, methylcellulose, polyyinylpyrrolidone, polyethylene glycol, polyvinyl alcohol and the like. Furthermore, macromolecules having pH-dependent solubility may also be used, and examples include carboxymethylethylcellulose, hydroxypropylmethylcellulose phthalate, hydroxypropylmethylcellulose acetate succinate, cellulose acetate phthalate, methacrylic acid copolymer and the like. Where the water-soluble macromolecules form a salt, any salts may be used. Two or more of the water-soluble macromolecules can be used in combination. The amount of the water-soluble macromolecules is not particularly limited, and may be appropriately chosen by those skilled in the art. For example, the amount may be 0.5 to 20 parts by weight, preferably 1 to 7 parts by weight based on the aforementioned substance as an active ingredient.

Methods for manufacturing the solid dispersion of the present invention are not particularly limited, and any methods that can be utilized as a method to prepare a solid dispersion may be applied. Specifically, examples include the solvent method (Chem. Pharm. Bull., 34 (8), 348 (1986)), the fusion method (J. Pharm. Sci., 59, 937 (1970)), the mixed grinding method (Yakuzaigaku, 45 (4), 291 (1985)), the spray drying method (Chem. Pharm. Bull., 44 (3), 568 (1996)) and the like. Among them, the solvent method is preferred. In the solid dispersion of the present invention, it is desirable that a substance selected form the group consisting of the sialic acid derivative represented by the aforementioned formula (I) and a salt thereof, and a hydrate thereof and a solvate thereof is dispersed in the aforementioned water-soluble macromolecule at the molecule level, and substantially loses crystalline property. Whether or not the substance is dispersed substantially in an amorphous state can be easily determined by, for example, measuring powder X ray diffraction of the solid dispersion.

When the solid dispersion of the present invention is manufactured by the solvent method, a substance selected form the group consisting of the sialic acid derivative represented by the aforementioned formula (I) and a salt thereof. and a hydrate thereof and a solvate thereof can be dissolved in a suitable solvent, and the solvent can be removed from the solution by a suitable method. The types of the solvents are not particularly limited so long as they can dissolve the aforementioned substance, and it is preferred to use an organic solvent having high volatility and low toxicity For example, ethanol, methanol, isopropanol, acetone and the like can be suitably used. Two or more of these solvents may be used in combination.

Methods to remove the solvent from the solution containing the aforementioned substance as an active ingredient and the water-soluble macromolecule dissolved therein are not particularly limited, and commonly used methods such as distillation by heating and vacuum distillation can be applied. After a solvent is removed, dried residue can be pulverized and sized by using a screen mill, hammer mill, jet mill or the like, and if necessary, the resulting product can be subjected to secondary drying and further sizing to produce a solid dispersion of the present invention. The aforementioned solution can also be spray-dried by using a spray dryer or the like, and the resulting product may optionally be subjected to secondary drying and then further sizing to produce a solid dispersion. Drying conditions may vary depending on a type of a water-soluble macromolecule. a solvent, or an apparatus be used, as well as to a type of the aforementioned substance as the active ingredient. Generally, the drying can be performed under heating at 200° C. and under ordinary pressure or high vacuum of 1 torr or less for several seconds to ten and several hours.

The solid dispersion of the present invention per se can be used as a medicament. Generally, however, a pharmaceutical formulation in the form of subtilized granule, granule, tablet, capsule, dry syrup or the like may be prepared and subjected to administration. The pharmaceutical preparation can be manufactured by subjecting the aforementioned solid dispersion to ordinary formulation processes such as, for example, mixing, granulation, sizing, tablet compression, coating, capsule filling and the like utilizing pharmaceutical manufacturing apparatuses. If necessary, a pharmaceutical composition may be prepared by using one or more suitable pharmaceutical additives, and then the pharmaceutical composition may be formulated in the aforementioned formulations.

The pharmaceutical additives include, for example, excipients (e.g., lactose, mannitol, crystalline cellulose, corn starch, potato starch etc.), disintegrating agents (e.g., sodium carboxymethyl starch, carboxymethylcellulose calcium, croscarmellose sodium, polyvinylpyrrolidone low substituted hydroxypropylcellulose, carboxymethylcellulose etc.), fluidization improving agents (e.g., light anhydrous silicic acid, hydrated silicon dioxide etc.), coloring agents (e.g., titanium oxide, yellow ferric oxide etc.), flavoring agents (e.g., tartaric acid, ascorbic acid. citric acid etc.), surface active agents (e.g., sodium laurylsulfate, polysorbate 80, polyethylene hydrogenated castor oil etc.), dispersing agents (e.g., crystalline cellulose, carboxyvinyl polymer etc.), lubricants (e.g., magnesium stearate etc.) and the like, and the amounts of these pharmaceutical additives can be suitably chosen by those skilled in the art. The pharmaceutical additives can be added during any one or more of the steps. For example, they may be added during the production of the solid dispersion, or during the steps of preparing the pharmaceutical preparation from the solid dispersion.

EXAMPLES

The present invention will be explained more specifically with reference to examples. However, the scope of the present invention is not limited to the following examples.

Example 1

5 g of 3 α-[N-(5-Acetamido-3,5-dideoxy-2-O-methyl-α-D-glycero-D-galacto-2-noneuropyranosonyl)amino] cholestane (hereinafter referred to as Compound A) and 15 g of hydroxypropylcellulose were dissolved in 2.5 liter of methanol and spray-dried at 140° C. by using a spray dryer. The resulting solid was subjected to vacuum dehydration at 70° C. for 6 hours using a vacuum desiccator, and sized through a 32# mesh sieve to obtain a solid dispersion.

Example 2

Compound A (1 g) and 5 g of polyvinylpyrrolidone were dissolved in 0.7 liter of ethanol. 0.3 g of light anhydrous silicic acid was then added to the solution and suspended, and then the solvent was removed by heating at 80° C. with stirring. The resulting solid was ground by using a grinding mill, subjected to vacuum dehydration at 70° C. for 6 hours, and sized through a 32# mesh sieve to obtain a solid dispersion. 3.78 g of polyvinylpyrrolidone was added to 1.26 g of this solid dispersion, and mixed in a conventional manner. The resulting mixture was suspended in 1000 ml of purified water to obtain a uniform suspension, of which concentration of Compound A was 1 mg/5 ml.

Example 3

Compound A (5 g) and 35 g of hydroxypropylcellulose were dissolved in 2.5 liter of methanol and spray-dried at 140° C. by using a spray dryer. The resulting solid was subjected to vacuum dehydration at 70° C. for 6 hours using a vacuum desiccator, and sized through a 32# mesh sieve to obtain a solid dispersion. This solid dispersion was dissolved in a 5% aqueous solution of sodium laurylsulfate to obtain a formulation in the form of a solution, of which concentration of Compound A was 5 mg/ml.

Example 4

Compound A (5 g) and 35 g of hydroxypropylcellulose were dissolved in 2.5 liter of methanol, and 20 g of polyvinylpyrrolidone was added and suspended in the solution. The suspension was then spray dried at 140° C. by using a spray dryer. The resulting solid was subjected to vacuum dehydration at 70° C. for 6 hours using a vacuum desiccator, and sized through a 32# mesh sieve to obtain a solid dispersion. This solid dispersion was filled into a capsule to obtain a formulation in the form of a capsule containing 5 mg of Compound A.

Example 5

12.0 g of the solid dispersion obtained in Example 4 was added with 6.06 g lactose, 5.6 g of sodium carboxymethyl starch, 4.2 g of hydrated silicon dioxide and 0.14 g of magnesium stearate, and the mixture was mixed and compressed into a tablet in a conventional manner to obtain a tablet containing 5 mg of Compound A.

Comparative Example

Compound A (5 g) and 15 g of hydroxypropylcellulose were mixed to obtain solid powder.

Comparative Example 2

Compound A (1 g), 5 g of polyvinylpyrrolidone and 0.3 g of light anhydrous silicic acid were mixed to obtain solid powder. 3.78 g of polyvinylpyrrolidone was added to 1.26 g of this solid powder, and mixed in a conventional manner. The resulting mixture was suspended in 1000 ml of purified water to obtain a uniform suspension, of which concentration of Compound A was 1 mg/5 ml.

Comparative Example 3

Compound A (5 g), 35 g of hydroxypropylcellulose and 20 g of polyvinylpyrrolidone were mixed to obtain solid powder. This solid powder was filled into a capsule to obtain a formulation in the form of a capsule containing 5 mg of Compound A.

Test Example 1

Residual solvent in each of the solid dispersions obtained in Examples 1, 2, 3 and 4 was measured by gas chromatography. As a result, the residual solvent in the solid dispersions obtained in Examples 1, 2, 3 and 4 was less than the detection limit (50 ppm).

Test Example 2

A dissolution test was performed for the solid dispersion and the solid powder obtained in Example 1 and Comparative Example 1, respectively. Each sample corresponding to 10 mg of Compound A was added to 100 ml of distilled water at 37° C. with stirring using a stirrer, and the solution was sampled after a given period. The dissolution amount of Compound A in the sampled solution was quantified. The results are shown in FIG. 1. The solid dispersion of Example 1 was found to have more superior dissolution property compared with the solid powder of Comparative Example 1.

Test Example 3

Figure 2:
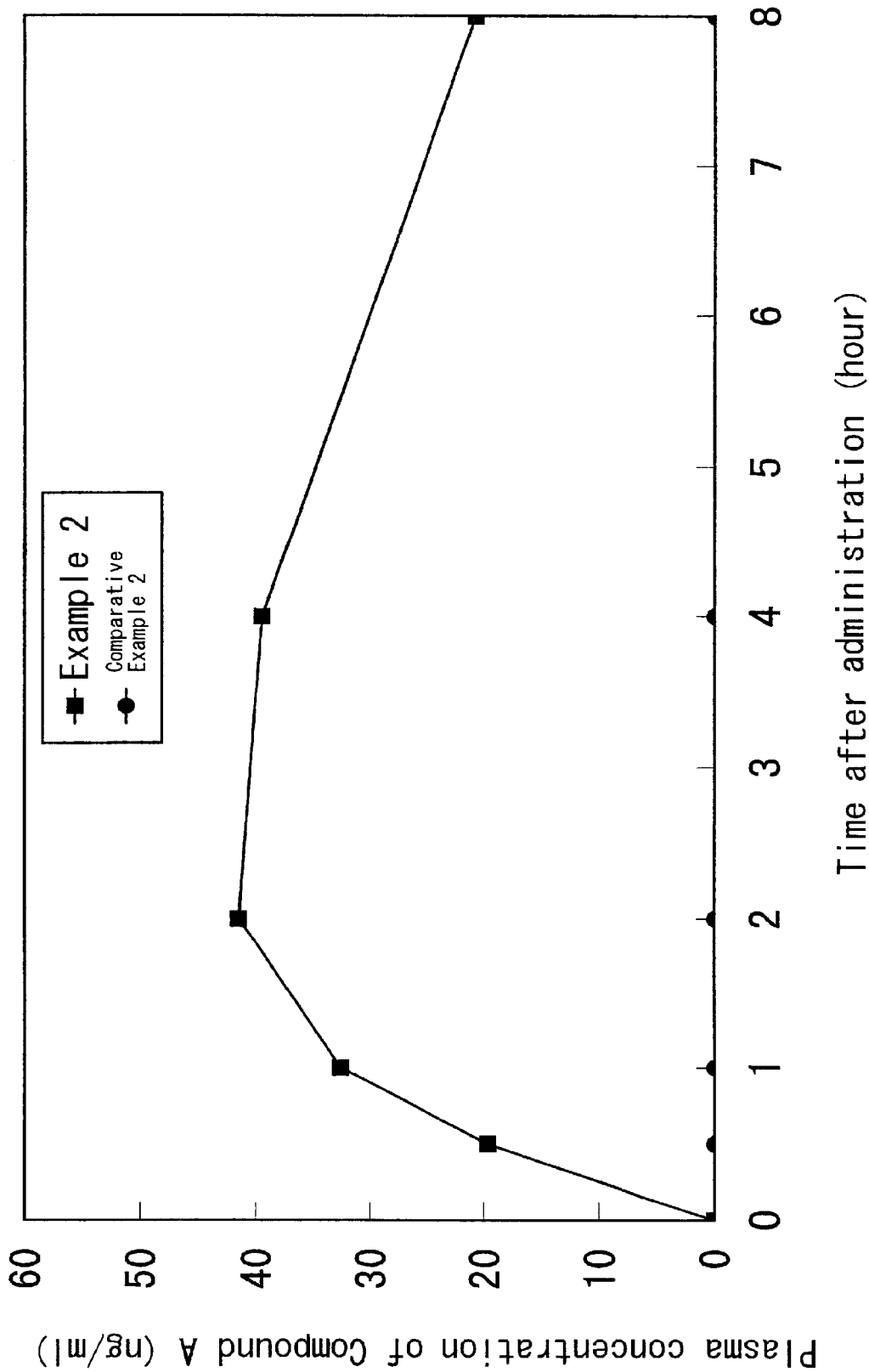
FIG. 2 shows results of an absorption test (rat) of a solid dispersion of the present invention. The results shown in the figure are averages of experiments performed in triplicate. The line with ■ represents the results obtained from a solid dispersion of the present invention (Example 2); and the line with □ from the suspension of Comparative Example 2.

Absorption tests were performed using rats for the suspensions obtained in Example 2 and Comparative Example 2. Compound A (1 mg/kg/5 ml of suspension) was forcibly administered to rats. Blood was collected after a given period, and plasma concentration of Compound A was quantified. The results are shown in FIG. 2. The suspension of the solid dispersion of Example 2 was found to have more superior absorption property compared with the suspension of the e solid powder of Comparative Example 2.

Test Example 4

Figure 3:
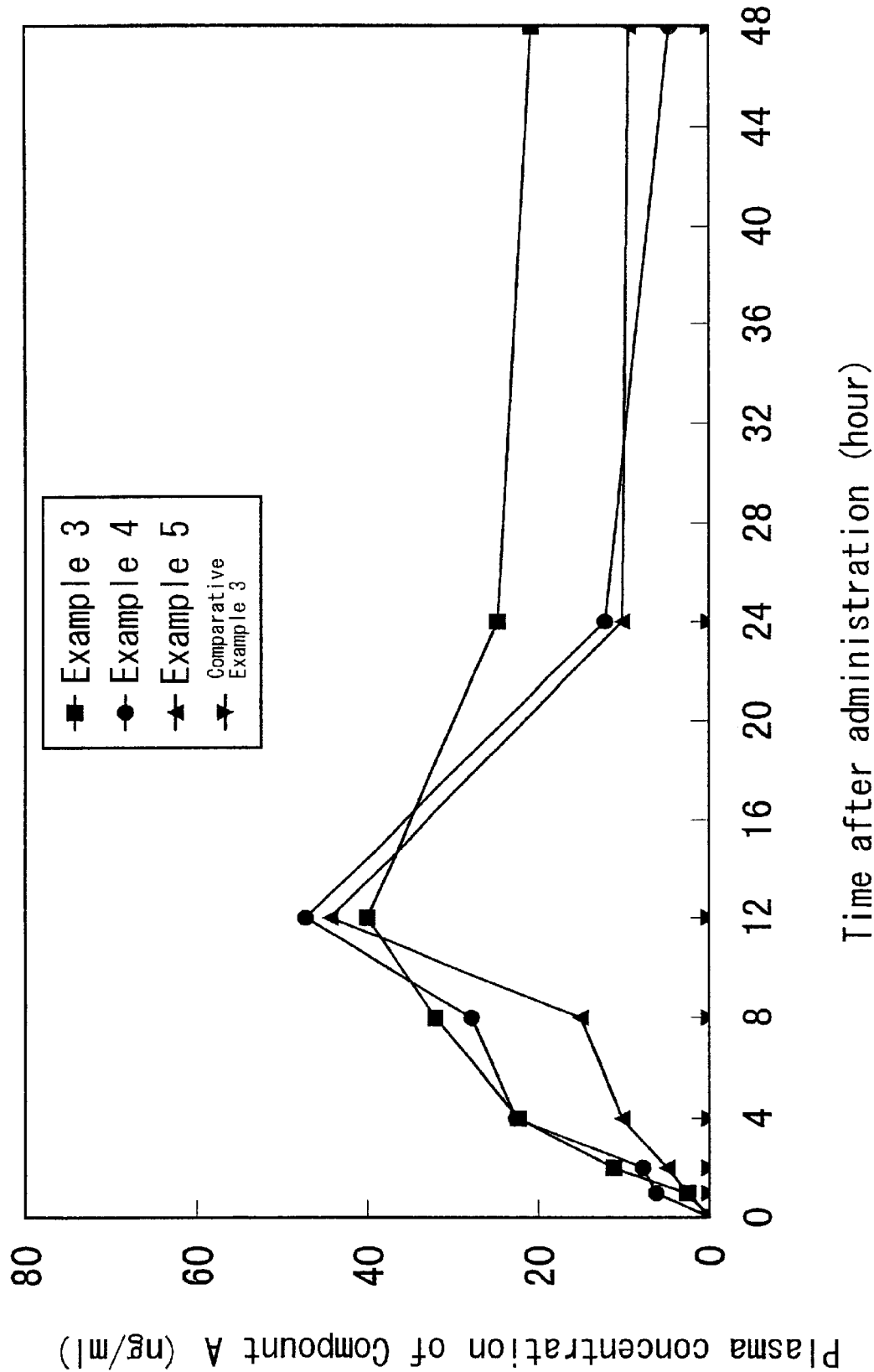
FIG. 3 shows results of an absorption test (dog) of solid dispersions of the present invention. The results shown in the figure are averages of experiments performed in triplicate. The line with □ represents the results obtained from a solid dispersion of the present invention (Example 3); the line with ♦ from a solid dispersion of the present invention (Example 4), the line with ● from a solid dispersion of the present invention (Example 5), and line with □ from the capsule (solid powder) of Comparative Example 3.

Absorption tests were performed using dogs for formulations obtained in Examples 3, 4, 5 and Comparative Example 3. Each formulation containing 5 mg of Compound A was forcibly administered to dogs. Blood was collected after a given period, and plasma concentration of Compound A was quantified. The results are shown in FIG. 3. The formulations of Examples 3, 4 and 5 were found to have more superior absorption properties compared with the capsule of Comparative Example 3.

Industrial Applicability

By using the solid dispersion of the present invention, solubiity and absorbability of the sialic acid derivatives of the formula (I) and sats thereof, which have superior efficacy a s medicaments, can be improved, and the problems accompanied with conventional methods, i.e., residual solvent, decomposition, contamination of foreign substances and the like, can be eliminated.

What is claimed is:

1. A solid dispersion which comprises a water-soluble macromolecule and a substance dispersed in the water-soluble macromolecule, wherein said substance is selected from the group consisting of a sialic acid derivative represented by the following general formula (I) and a salt thereof, and a hydrate thereof and a solvate thereof:

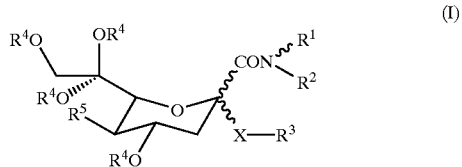

[in the above general formula (I), $R^1$ represents a steroid compound residue, $R^2$ represents hydrogen atom or a $C_1$–$C_4$ alkyl group, $R^3$ represents a $C_1$–$C_{15}$ alkyl group,

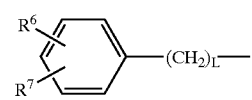

{in the formula, $R^6$ and $R^1$ independently represent hydrogen atom, a halogen atom, a $C_1$–$C_4$ alkyl group, hydroxyl group, $R^8O$— (in the formula, $R^8$ represents a $C_1$–$C_4$ alkyl group, phenyl group or a phenyl-($C_1$–$C_3$) alkyl group), nitro group, amino group, a $C_1$–$C_4$ alkylamino group, a $C_2$–$C_8$ dialkylamino group or $R^9O$—CO— (in the formula, $R^9$ represents hydrogen atom, a $C_1$–$C_4$ alkyl group, phenyl group or a phenyl-($C_1$–$C_3$) alkyl group), and symbol "L" represents an integer of from 0 to 6}, $R^{10}O(CH_2)_m$— (in the formula, $R^{10}$ represents hydrogen atom; a $C_1$–$C_4$ alkyl group; a phenyl group which may have one or more substituents selected from the group consisting of a $C_1$–$C_4$ alkyl group, a halogen atom, hydroxyl group, nitro group, amino group, and a carboxyl group; or a phenyl-($C_1$–$C_3$) alkyl group which may have one or more substituents selected from the group consisting of a $C_1$–$C_4$ alkyl group, a halogen atom, hydroxyl group, nitro group, amino group, and carboxyl group, and symbol "m" represents an integer of from 2 to 6), or $(R^{11})(R^{12})N$—$(CH_2)_n$— {in the formula, $R^{11}$ represents hydrogen atom or a $C_1$–$C_4$ alkyl group, $R^{12}$ represents hydrogen atom; a $C_1$–$C_4$ alkyl group; a $C_2$–$C_7$ acyl group; a $C_1$–$C_4$ alkylsulfonyl group a phenylsulfonyl group which may have one or more substituents selected from the group consisting of a $C_1$–$C_4$ alkyl group, halogen atom, hydroxyl group, nitro group, amino group, and a carboxyl group; or $R^{13}O$—CO— (in the formula, $R^{13}$ represents a $C_1$–$C_4$ alkyl group, phenyl group or a phenyl-($C_1$–$C_3$) alkyl group) and symbol "n" represents an integer of from 2 to 6}, $R^4$ represents hydrogen atom or a $C_2$–$C_7$ acyl group, $R^5$ represents $R^{14}O$— (in the formula, $R^{14}$ represents hydrogen atom or a $C_2$–$C_7$ acyl group) or $R^{15}NH$— {in the formula, $R^{15}$ represents a $C_2$–$C_7$ acyl group; $R^{16}O(CH_2)_p$—CO— (in the formula, $R^{16}$ represents hydrogen atom, a $C_1$–$C_6$ alkyl group, phenyl group, or a phenyl-($C_1$–$C_3$) alkyl group, and p represents an integer of from 0 to 4); a $C_7$–$C_{11}$ aroyl group which may have one or more substituents selected from the group consisting of a $C_1$–$C_4$ alkyl group, a halogen atom, hydroxyl group, nitro group, amino group, and a carboxyl group; a phenyl-($C_1$–$C_3$) alkylcarbonyl group which may have one or more substituents selected from the group consisting of a $C_1$–$C_4$ alkyl group, a halogen atom, hydroxyl group, nitro group, amino group, and a carboxyl group; a $C_1$–$C_4$ alkylsulfonyl group; or a phenylsulfonyl group which may have one or more substituents selected from the group consisting of a $C_1$–$C_4$ alkyl group, a halogen atom, hydroxyl group, nitro group, amino group, and a carboxyl group}, and X represents an oxygen atom or a sulfur atom].

2. The solid dispersion according to claim 1 which comprises the substance selected from the group consisting of the sialic acid derivative wherein $R^1$ is:

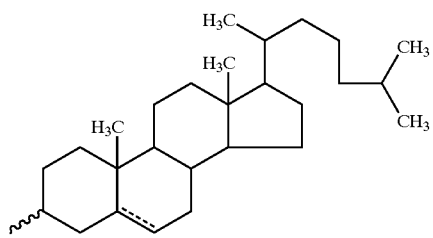

(in the formula, ═══ represents a single bond or a double bond) and a salt thereof, and a hydrate thereof and a solvate thereof.

3. The solid dispersion according to claim, 1 which comprises the substance selected from the group consisting of the sialic acid derivative wherein $R^1$ is:

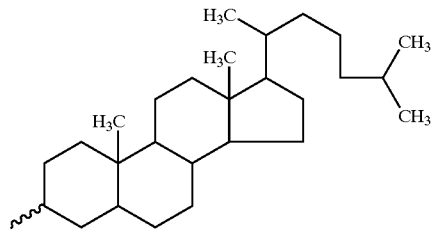

and a salt thereof, and a hydrate thereof and a solvate thereof.

4. The solid dispersion according to claim 1 which comprises the substance selected from the group consisting of the sialic acid derivative wherein $R^1$ is:

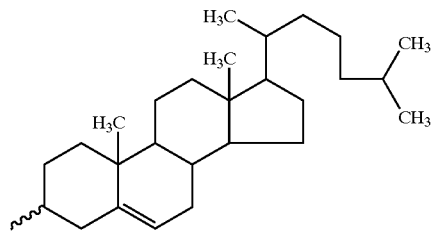

and a salt thereof, and a hydrate thereof and a solvate thereof.

5. The solid dispersion according to claim 1 which comprises the substance selected from the group consisting of the sialic acid derivative wherein $R^2$ is hydrogen atom or methyl group and a salt thereof, and a hydrate thereof and a solvate thereof.

6. The solid dispersion according to claim 1 which comprises the substance selected from the group consisting of the sialic acid derivative wherein $R^2$ is hydrogen atom and a salt thereof, and a hydrate thereof and a solvate thereof.

7. The solid dispersion according to claim 1 which comprises the substance selected from the group consisting of the sialic acid derivative wherein $R^3$ is a $C_1$–$C_8$ alkyl group,

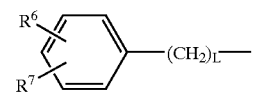

{in the formula, $R^6$ and $R^7$ independently represent hydrogen atom, a halogen atom, or $R^9O$—CO— (in the formula, $R^9$ represents hydrogen atom or a $C_1$–$C_4$ alkyl group), and symbol "L" represents an integer of from 0 to 3}, $R^{10}O$ $(CH_2)_m$— (in the formula, $R^{10}$ represents hydrogen atom, a $C_1$–$C_4$ alkyl group, phenyl group, or a phenyl-($C_1$–$C_3$) alkyl group, and symbol "m" represents an integer of from 2 to 4), or $(R^{11})(R^{12})N$—$(CH_2)_n$— {in the formula, $R^{11}$ represents hydrogen atom, $R^{12}$ represents hydrogen atom, a $C_2$–$C_7$ acyl group, a $C_1$–$C_4$ alkylsulfonyl group or $R^{13}O$—CO— (in the formula, $R^{13}$ represents a phenyl-($C_1$–$C_3$) alkyl group) and symbol "n" represents an integer of from 2 to 4} and a salt thereof, and a hydrate thereof and a solvate thereof.

8. The solid dispersion according to claim 1 which comprises the substance selected from the group consisting of the sialic acid derivative wherein $R^3$ is a $C_1$–$C_8$ alkyl group or

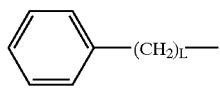

(in the formula, symbol "L" represents an integer of from 0 to 3) and a salt thereof, and a hydrate thereof and a solvate thereof.

9. The solid dispersion according to claim 1 which comprises the substance selected from the group consisting of the sialic acid derivative wherein $R^3$ is a $C_1$–$C_3$ alkyl group and a salt thereof, and a hydrate thereof and a solvate thereof.

10. The solid dispersion according to claim 1 which comprises the substance selected from the group consisting of the sialic acid derivative wherein $R^4$ is hydrogen atom or acetyl group and a salt thereof, and a hydrate thereof and a solvate thereof.

11. The solid dispersion according to claim 1 which comprises the substance selected from the group consisting of the sialic acid derivative wherein $R^4$ is hydrogen atom and a salt thereof, and a hydrate thereof and a solvate thereof.

12. The solid dispersion according to claim 1 which comprises the substance selected from the group consisting of the sialic acid derivative wherein $R^5$ is $R^{14}O$— (in the formula, $R^{14}$ represents hydrogen atom or acetyl group) or $R^{15}NH$— {in the formula, $R^{15}$ represents a $C_2$–$C_7$ acyl group, $R^{16}O(CH_2)_p$—CO— (in the formula, $R^{16}$ represents hydrogen atom, a $C_1$–$C_4$ alkyl group or a phenyl-($C_1$–$C_3$) alkyl group, and symbol "p" represents an integer of from 0 to 4), a $C_7$–$C_{11}$ aroyl group, a $C_1$–$C_3$ alkylsulfonyl group or a phenylsulfonyl group} and a salt thereof, and a hydrate thereof and a solvate thereof.

13. The solid dispersion according to claim 1 which comprises the substance selected from the group consisting of the sialic acid derivative wherein $R^5$ is $R^{14}O$— (in the formula, $R^{14}$ represents hydrogen atom) or $R^{15}NH$— {in the formula, $R^{15}$ represents a $C_2$–$C_5$ acyl group, $R^{16}O$— $(CH_2)_p$—CO— (in the formula, $R^{16}$ represents hydrogen atom and symbol "p" represents 1)} and a salt thereof, and a hydrate thereof and a solvate thereof.

14. The solid dispersion according to claim 1 which comprises the substance selected from the group consisting of the sialic acid derivative wherein $R^5$ is $R^{15}NH$— (in the formula, $R^{15}$ represents acetyl group) and a salt thereof, and a hydrate thereof and a solvate thereof.

15. The solid dispersion according to claim 1 which comprises the substance selected from the group consisting of the sialic acid derivative wherein X is oxygen atom and a salt thereof, and a hydrate thereof and a solvate thereof.

16. The solid dispersion according to claim 1 wherein the sialic acid derivative is 3 α-[N-(5-acetamido-3,5-dideoxy-2-O-methyl-α-D-glycero-D-galacto-2-noneuropyranosonyl)amino]cholestane.

17. The solid dispersion according claim 1 which comprises said substance in substantially amorphous state.

18. A pharmaceutical composition comprising the solid dispersion according to claim 1 and a pharmaceutically acceptable carrier.

* * * * *

UNITED STATES PATENT AND TRADEMARK OFFICE
CERTIFICATE OF CORRECTION

PATENT NO.   : 6,444,649 B1  Page 1 of 1
DATED        : September 3, 2002
INVENTOR(S)  : T. Inamori et al.

It is certified that error appears in the above-identified patent and that said Letters Patent is hereby corrected as shown below:

<u>Column 13,</u>
Line 17, after "alkylsulfonyl group" insert -- ; --.

Signed and Sealed this

Third Day of June, 2003

JAMES E. ROGAN
*Director of the United States Patent and Trademark Office*